United States Patent [19]

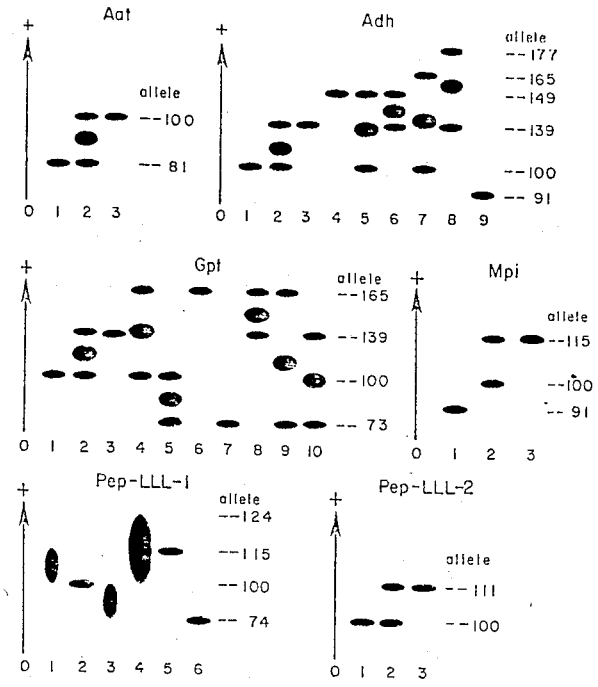
Aat
allele
--100
-- 81
0 1 2 3
Adh
allele
--177
--165
--149
--139
--100
-- 91
0 1 2 3 4 5 6 7 8 9
Gpt
allele
--165
--139
--100
-- 73
0 1 2 3 4 5 6 7 8 9 10
Mpi
allele
--115
--100
-- 91
0 1 2 3
Pep-LLL-1
allele
--124
--115
--100
-- 74
0 1 2 3 4 5 6
Pep-LLL-2
allele
-- 111
--100
0 1 2 3

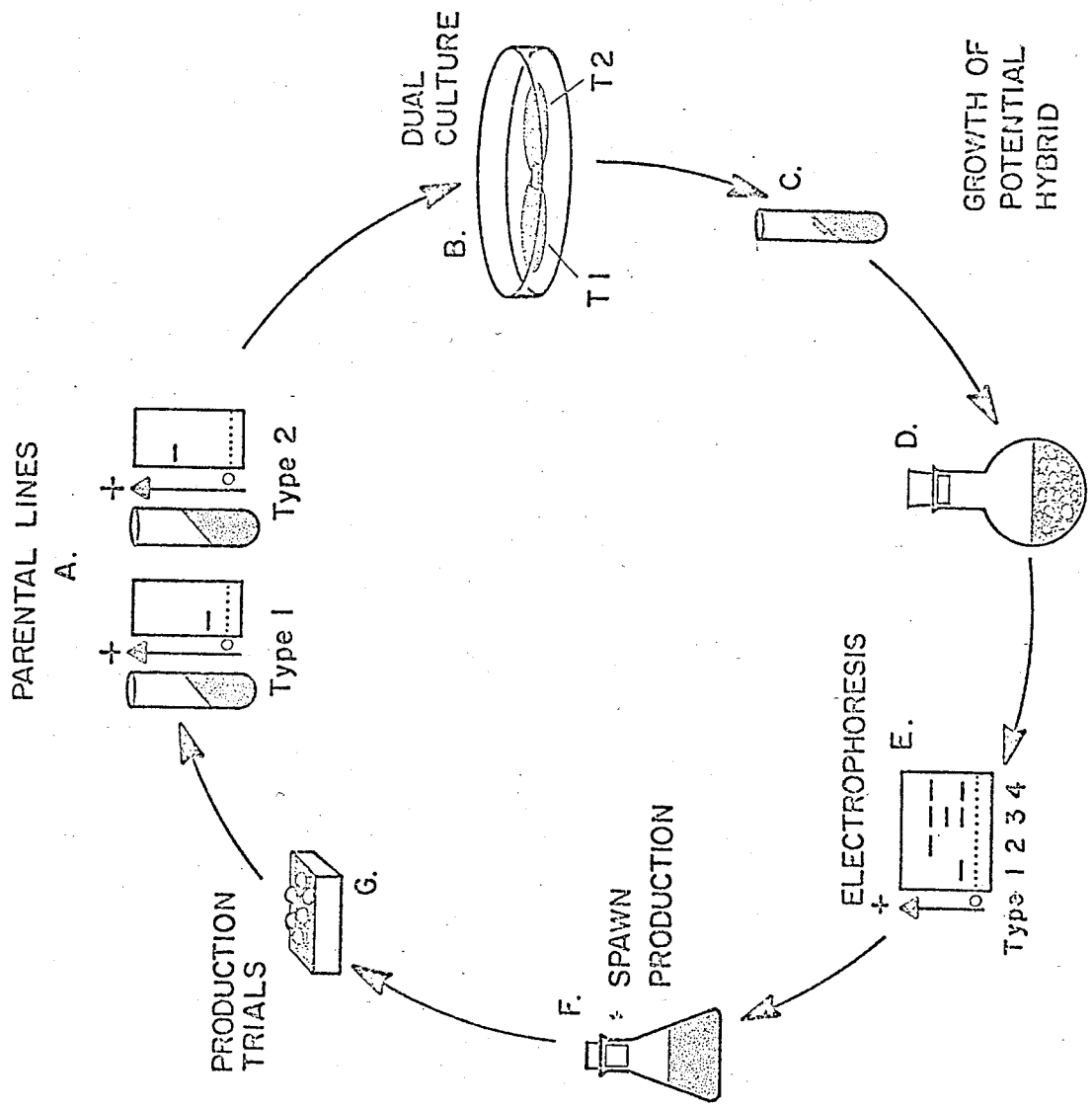
PARENTAL LINES
A.
Type 1
Type 2
DUAL CULTURE
B.
T1
T2
C.
GROWTH OF POTENTIAL HYBRID
D.
E.
ELECTROPHORESIS
Type 1 2 3 4
F.
SPAWN PRODUCTION
G.
PRODUCTION TRIALS

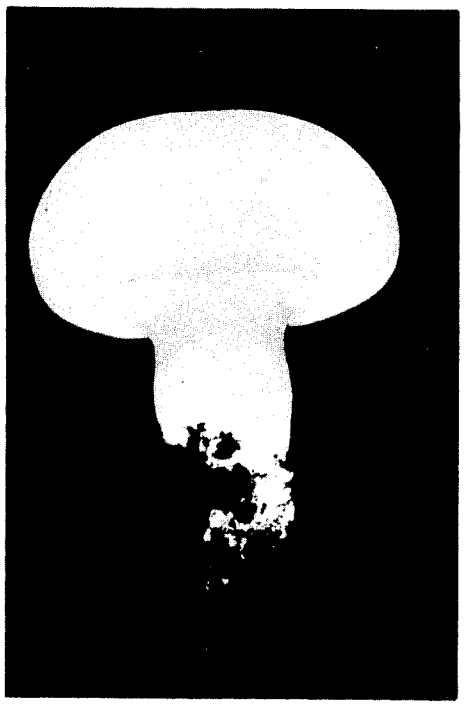
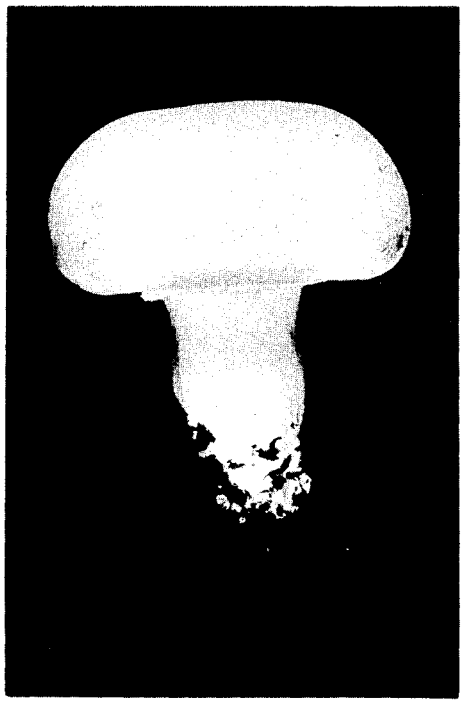

Royse et al.

[11] Patent Number: Plant 5,773

[45] Date of Patent: Jul. 22, 1986

[54] MUSHROOM PLANT

[75] Inventors: Daniel J. Royse, State College, Pa.; Bernard P. May, Groton, N.Y.

[73] Assignee: Research Corporation, New York, N.Y.

[21] Appl. No.: 663,099

[22] Filed: Oct. 19, 1984

[51] Int. Cl.[4] ..... A01H 15/00

[52] U.S. Cl. ..... Plt./89

[58] Field of Search ..... Plt./89

*Primary Examiner*—Robert E. Bagwill

*Attorney, Agent, or Firm*—Scully, Scott, Murphy & Presser

[57] ABSTRACT

A new and distinct variety of mushroom is described. This variety is similar to a type called "smooth white" in the trade. The new variety possesses advantages in both yield and size when compared to three commercially available lines 303, 310 and 348. The new variety also displays a unique electrophoretic isozyme phenotype.

4 Drawing Figures

1

The present invention relates to a new and distinct line (strain) of *Agaricus brunnescens* Peck [=*A. bisporus* (Lange) Imbach].

No other major commercially important crop has experienced as little genetic improvement as the common edible mushroom, *Agaricus brunnescens* Peck. [=*Agaricus bisporus* (Lange) Imbach]. This situation has been due exclusively to the unique genetic life history of this fungus which hinders and often precludes manipulation of the germ plasm without the use of specific codominant markers. Unlike other *Agaricus* spp., *Agaricus brunnescens* is primarily two-spored.

Selective breeding programs for *A. brunnescens* have been proposed which utilize auxotrophic mutants (Raper and Raper, *Mush. Sci.* 8:1-9 (1972)); Raper et al., *Mycologia* 64:1088-1172, (1972)), mycelial fusion and nuclear exchange between heterokaryotic lines (Moessner, *Mush. Sci.* 5:197-203 (1962)), multispore-derived cultures (Stubnya, *Mush. Sci.* 10(1):83-89 (1979)), or resistance to biocides (Elliott,*Mush. Sci.* 10(1):73-81 (1979)). Each of these approaches has the disadvantage that a limited number of crosses can be made, corroborated, and uniquely marked.

Isozyme analysis has proven to be a potent genetic tool because of the interpretable, one-to-one relationship of isozyme phenotype to the organism's genotype. The single-gene basis of observed electrophoretic variation in fungi by the use of single-spore-derived isolates has been shown for *Conidiobolus thromboides* Dreschler [syn, *Entomophthora virulenta* Hall et Dunn] (May et al. *Exp. Mycol* 3:289-297 (1979)), *Agaricus campestris* (May and Royse *Mush.Sci.* 11(2):799-817 (1981); and *Biochem. Genet.* 20:1165-1173, (1982)), and *A. Brunnescens* (May and Royse supra (1981); and Royse and May *Mycologia* 74:93-102 (1982). For *A. brunnescens* isozyme analysis allows the ability to distinguish homokaryotic from heteroakaryotic single-spore-drived lines.

On the basis of five variable biochemical loci Royse and May, (supra, 1982) were able to partition lines of *A. brunnescens* into genotypic classes. Combining the number of genotypes possible at each locus would allow over 20,000 recognizable genotypic classes. The finding of only five genotypic classes among 34 commercial lines and only 27 classes in 162 lines in The Pennsylvania State University Mushroom Culture Collection is further evidence that little of the potential genotypic variability is expressed in the stocks examined.

2

This new line was produced as a result of the breeding program in the Department of Plant Pathology, The Pennsylvania State University. The invention was completed in two major phases: (1) crossing of two compatible breeding stocks (homokaryons) and (2) evaluation of desirable cultivation characteristics of the new hybrid. The new line was produced by crossing homokaryons derived from a golden white parent ($D_{26}$) commonly used in cave culture and a smooth white parent (L81WB) commonly used for commercial cultivation. The improved characteristic of this mushroom line is its increased yield in $Kg/m^2$ as compared to the yield and size of other commercially available lines.

The *A. brunnescens* isolates (D26 and L81WB) were from The Pennsylvania State University Mushroom Culture Collection (PSUMCC). The novel hybrid line was produced by crossing homokaryons derived from a golden white parent ($D_{26}$, commonly used in cave culture) and from a smooth white parent (L81WB, commonly used for commercial cultivation). The parental lines have been electrophoretically typed by Royse and May (supra, 1982) and May and Royse (supra, 1982). Allelic variability observed in the PSUMCC is diagramatically represented in FIG. 1. The alleles for lines $D_{26}$ and L81WB at six bioichemical loci are listed in TABLE 1.

Homokaryons were derived from lines $D_{26}$ and and L81WB and used as breeding stock. The general scheme followed that presented in FIG. 2. The alleles for the breeding stock homokaryons ($D_{26/114}$ and L81WB/503) are listed in TABLE 2. Breding stocks $D_{26/114}$ and L81WB/503 were set up in dual culture as outlined by May and Royse (*Exp. Mycol.* 6:283-292(1982)) and as depicted in FIG. 2. The alleles possessed by the resulting hybrid are listed in TABLE 3. The hybrid's allelic combination is unique to any commercial or PSUMCC isolates and can be easily distinguished from any of these isolates.

Mushroom hybrid BB13-1 is of a type similar to one called "smooth white" in the trade such as Darlington 91. The cap is smooth and "pure white" in color. Normally, this mushroom is colored pure white and is smooth with no scaliness; however, under drought conditions or relatively high air movement the caps may become slightly scaly and colored creamish-white. At maturity the cap frequently is domed. The caps of this mushroom line are thicker than the typical "pure white" mushrooms.

The cap or pileus of the mushroom, when the veil breaks, varies between 24–150 mm in diameter and is of generally convex shape.

The stipe is 25–80 mm long, 8–25 mm thick, strongly bulbous in the button stage but becoming cylindrical at maturity.

The lamellae are whitish at first but become a pinkish flesh color by the time the veil breaks. Later the gills become a purplish brown and finally a chocolate brown as the spores mature. The gills are free, crowded, conspicuously white-marginate, with lamellulae interspersed.

The annulus is prominent and fairly persistent, composed of a single type, formed from a velar sheath over the stipe extending up to the margins of the unexpanded pileus.

The flesh is white, turning bright pinkish red in approximately 2 minutes when cut or bruised (particularly in the stipe) and later turning brown. The flesh is quite thick below the disc.

The pileus cuticle is composed of radially arranged, repent, parallel to interwoven, clampless, hyaline to creamish hyphae measuring 2.5–12 μm diameter. The pielus trama is composed of large, thin-walled, interwoven, clampless hyphae measuring 4–32 μm diameter. Pleurocystidia are lacking. Cheilocystidia are abundant and form a continuous sterile tissue, clavate to cylindrical or fusoid, often rather irregular in shape, not clamped at the base, and measuring 14–35×5.5–14 μm. The basidia are mostly 2-spored (rarely 2, 3, or 4-spored), clavate, not clamped at the base, and measure 18–36×6–8 μm. The basidiospores are broadly elliptical to slightly ovate in face view, unilaterally flattened-elliptical to -ovate in side view, smooth, thick- or thin-walled, lacking a germ pore, dark brown in mass, and measure 6.1–9.2×4.6–7.0 μm.

Evaluations of the hybrid's characteristics for commercial desirability were performed at the Mushroom Research Center of The Pennsylvania State University, University Park, Pa. The hybrid was subjected to five crop evaluations on four different composts using commercial lines for comparisons. A summary of the results are presented in Tables 4, 5, and 6. As can be seen from these tables BB13-1 is superior in yield to the commercial lines examined (Tables 4, 5, and 6). In all five evaluations the novel line was significantly more productive than the commercial lines (303, 310, 348).

Mushroom size was significantly greater for BB13-1 than for the commercial line 310 (Table 6). There was no significant difference in size between lines 348 and the hybrid (Table 5) and between 303 and the hybrid (Table 6). In summary, the newly developed lines demonstrates advantages in both yield and size when compared to three commercially used lines (303, 310 and 348).

BRIEF DESCRIPTION OF THE FIGURES

FIG. 1 illustrates the allelic variability of *Agaricus brunnescens* cultures from The Pennsylvania State University Mushroom Culture Collection and from commercial spawn makers.

FIG. 2 illustrates a strategy for confirmation of hybridization and subsequent hybrid evaluation in the common cultivated mushroom.

a. Selection from germ plasm bank of parental breeding stock with alternate electrophoretic types.

b. Dual culture of parental lines on agar plates.

c. Selection of possible hybrid mycelium from interaction zone.

d. Culture of selection in liquid medium.

e. Electrophoretic confirmation of hybrid; types 1 and 2=parental lines; type 3=hybrid (note "extra" band); type 4-mix only of parental lines.

f. Production of spawn from confirmed hybrids for spawning compost.

g. Selection among different hybrid lines for desirable traits.

FIG. 3 is a photograph showing two forms of the mushroom plants of the subject invention.

TABLE 1.

Alleles possessed by the parental lines used to derive homokaryotic breeding stock for hybrid production.

| | BIOCHEMICAL LOCI | | | | | |
|---|---|---|---|---|---|---|
| Line No. | Gpt | Mpi | Pep-LLL-1 | Pep-LLL-2 | Adh | Aat |
| $D_{26}$ | 100/165 | ∅[a] | 100/115 | 100/100 | 100/149 | 81/100 |
| L81WB | 100/100 | ∅ | 100/115 | 100/111 | 100/100 | 81/100 |

[a]No activity.

TABLE 2.

Alleles possessed by homokaryotic breeding stock for hybrid production.

| | BIOCHEMICAL LOCI | | | | | |
|---|---|---|---|---|---|---|
| Line No. | Gpt | Mpi | Pep-LLL-1 | Pep-LLL-2 | Adh | Aat |
| $D_{26/114}$ | 100 | ∅[a] | 115[b] | 100 | 149 | 81 |
| L81WB/503 | 100 | ∅ | 115 | 111 | 100 | 100 |

[a]No activity.
[b]The homomer is not functional and, therefore, no enzyme activity is observed in extracts of lines homozygous for allele 115.

TABLE 3

Alleles possessed by novel hybrid as a result of crossing homokaryotic breeding stock.

| | BIOCHEMICAL LOCI | | | | | |
|---|---|---|---|---|---|---|
| Line No. | Gpt | Mpi | Pep-LLL-1 | Pep-LLL-2 | Adh | Aat |
| BB13-1 (Hybrid) | 100/100 | ∅[a] | 115/115[b] | 100/111 | 100/149 | 81/100 |

[a]No activity.
[b]The homomer is not functional and, therefore, no enzyme activity is observed in extracts of lines homozygous for allele 115.

TABLE 4

Effect of air temperatures (18° or 24° C.) during production on total yield of selected isolates of *Agaricus brunnescens* and *A. bitorquis* for 3 crops.

| Crop I | | Crop II | | Crop III | |
|---|---|---|---|---|---|
| Temp and isolate | Mean total yield (g) | Temp and isolate | Mean total yield (g) | Temp and isolate | Mean total yield (g) |
| At 18° C. | | At 18° C. | | At 18° C. | |
| BB-13-1 | 5247a[y] | BB-131-1 | 5207a | BB-13-1 | 6748a |
| BB-32-3 | 4934a | BB-19-1 | 4395b | L81 | 4941b |
| BB-34-2 | 4071bc | BB-32-3 | 4358b | D26 | 4928b |
| 28-549 | 4042c | 310 | 3726c | 310 | 3560cd |
| 310 | 1291c | BB-34-2 | 3588c | K46[x] | 2329d |
| At 24° C. | | At 24° C. | | At 24° C. | |
| BB-13-1 | 4664ab | BB-19-1 | 3924bc | K46[x] | 4816b |
| BB-34-2 | 3799c | BB-13-1 | 3641c | BB-13-1 | 4116c |
| BB-32-3 | 3692c | BB-34-2 | 2576d | L81 | 1991e |
| 28-549 | 2020d | BB-32-3 | 2282d | D26 | 1250f |

TABLE 4-continued

Effect of air temperatures (18° or 24° C.) during production on total yield of selected isolates of *Agaricus brunnescens* and *A. bitorquis* for 3 crops.

| Crop I | | Crop II | | Crop III | |
|---|---|---|---|---|---|
| Temp and isolate | Mean total yield (g) | Temp and isolate | Mean total yield (g) | Temp and isolate | Mean total yield (g) |
| 310 | 712e | 310 | 1576e | 310 | 750f |

[z]Mean yield of 6 replicates 0.36 $m^2$ production surface area per replicate.

[y]Means followed by the same letter within the same column are not significantly different based on the Waller-Duncan K-Ratio T-Test at P = 0.05.

[x]Commercial line of *Agaricus bitorquis*.

TABLE 5.

Relative yield and size of novel hybrid mushroom (BB13-1) and a commercially used off-white variety (348).

| Isolate | Mean total yield (g) | Mean size (g) |
|---|---|---|
| BB13-1 (Hybrid) | 5550a[x] | 5.4a |

TABLE 5.-continued

Relative yield and size of novel hybrid mushroom (BB13-1) and a commercially used off-white variety (348).

| Isolate | Mean total yield (g) | Mean size (g) |
|---|---|---|
| 348 | 4835b | 5.7a |

[x]Means followed by the same letter within the same column are not significantly different based on the Waller-Duncan K-Ratio T-test at P = 0.05.

TABLE 6.

Relative yield and size of novel hybrid mushroom (BB13-1) and commercially used smooth white varieties (310 and 303) either nonsupplemented or supplemented with delayed release nutrient.

| | Mean total yield (g) | | Mean size (g) | |
|---|---|---|---|---|
| Isolate | Nonsupplemented | Supplemented | Nonsupplemented | Supplemented |
| BB13-1 (Hybrid) | 5894a[x] | 7564a | 4.5a | 4.9a |
| 310 | 5169b | 6481b | 3.8b | 4.3b |
| 303 | 4917b | 6151b | 4.8a | 4.7a |

[x]Means followed by the same letter within the same column are not significantly different based on the Waller-Duncan K-Ratio T-test at P = 0.05.

What is claimed is:

1. A new and distinct variety of mushroom substantially as shown and described characterized particularly as to novelty by its greater productivity and yield when compared to three commercially available lines 303, 310 and 348 and by its unique electrophoretic isozyme phenotype.

* * * * *